(12) United States Patent
Shkarupa et al.

(10) Patent No.: US 11,504,220 B2
(45) Date of Patent: Nov. 22, 2022

(54) LIGATURE DELIVERY SYSTEM FOR AXIAL FIXATION OF PELVIC FLOOR STRUCTURES IN PELVIC ORGAN PROLAPSE AND STRESS URINARY INCONTINENCE REPAIR

(71) Applicant: LIMITED LIABILITY COMPANY "LINTEX", Saint-Petersburg (RU)

(72) Inventors: Dmitrii Dmitrievich Shkarupa, Saint-Petersburg (RU); Valeriy Anatolievich Zhukovskiy, Saint-Petersburg (RU); Tatiana Sergeevna Filipenko, Saint-Petersburg (RU); Aleksandra Nikitichna Zhukovskaya, Saint-Petersburg (RU); Andrei Sergeevich Shulgin, Saint-Petersburg (RU); Nikita Dmitrievich Kubin, Saint-Petersburg (RU); Gleb Valerevich Kovalev, Saint-Petersburg (RU)

(73) Assignee: LIMITED LIABILITY COMPANY "LINTEX", Saint-Petersburg (RU)

( * ) Notice: Subject to any disclaimer, the term of this patent is extended or adjusted under 35 U.S.C. 154(b) by 0 days.

(21) Appl. No.: 17/284,731

(22) PCT Filed: Jan. 21, 2021

(86) PCT No.: PCT/RU2021/050012
§ 371 (c)(1),
(2) Date: Apr. 12, 2021

(87) PCT Pub. No.: WO2021/246912
PCT Pub. Date: Dec. 9, 2021

(65) Prior Publication Data
US 2022/0183813 A1 Jun. 16, 2022

(30) Foreign Application Priority Data
Jun. 2, 2020 (RU) .......................... RU2020118060

(51) Int. Cl.
*A61F 2/00* (2006.01)
(52) U.S. Cl.
CPC .... *A61F 2/0063* (2013.01); *A61F 2002/0068* (2013.01); *A61F 2210/0004* (2013.01)
(58) Field of Classification Search
CPC ...................... A61F 2/0063; A61F 2002/0068
See application file for complete search history.

(56) References Cited

U.S. PATENT DOCUMENTS

| 2005/0070930 A1* | 3/2005 | Kammerer | ............ A61F 2/0063 606/151 |
| 2007/0282160 A1* | 12/2007 | Sheu | ..................... A61L 31/148 600/30 |

\* cited by examiner

*Primary Examiner* — John P Lacyk
(74) *Attorney, Agent, or Firm* — Nadya Reingand

(57) ABSTRACT

The invention relates to medicine, in particular, to gynecology and urology, namely, to for ligature delivery system for axial fixation of pelvic floor structures in pelvic organ prolapse and stress urinary incontinence. Ligature delivery system for axial fixation of pelvic floor structures in pelvic organ prolapse and stress urinary incontinence consisting of the mesh material that is woven from a non-biodegradable and biodegradable monofilament threads, according to the invention so that non-biodegradable threads are arranged along to the implant axis and are not linked with each other. The technical effect is providing the axial support that is physiological for apical structures of pelvic floor and minimizing risks of mesh-associated postsurgical complications.

1 Claim, 2 Drawing Sheets

LIGATURE DELIVERY SYSTEM FOR AXIAL FIXATION OF PELVIC FLOOR STRUCTURES IN PELVIC ORGAN PROLAPSE AND STRESS URINARY INCONTINENCE REPAIR

FIELD OF INVENTION

The invention relates to medicine, in particular, to gynecology and urology, namely, to a ligature delivery system for axial fixation of pelvic floor structures in pelvic organ prolapse (hereinafter—«POP») and stress urinary incontinence (hereinafter—«SUI») repair.

BACKGROUND

POP is a condition developing due to a loss of a normal support of uterus, bladder or rectum with pelvic floor structures and leading to descent of one or more organs into vagina or beyond it (Haylen B. T., de Ridder D., Freeman R. M. et al. An International Urogynecological Association (IUGA)/International Continence Society (ICS) joint report on the terminology for female pelvic floor dysfunction. Int Urogynecol J. 2010; 21:5-26). Herewith, a prolapse in anterior and apical compartment are the most wide spread, which is met twice as frequently as posterior pelvic floor compartment (Barber M. D., Maher C. Epidemiology and outcome assessment of pelvic organ prolapsed. Int Urogynecol J. 2013; 24:1783-1790). The generally accepted main etiologic reason for developing POP is incompetence of attachments supporting pelvic organs.

SUI is a pathology associated with incompetence of attachments supporting urethra in an optimal condition providing urinary retention at increase of abdominal pressure. It is a wide spread social and economic problem. According to available data, up to 30% women in the world suffer from urinary incontinence (Fultz N. H., Burgio K., Diokno A. C., Kinchen K. S., Obenchain R., Bump R. C. Burden of stress urinary incontinence for community-dwelling women. Am J Obstet Gynecol. 2003; 189(5):1275-1282).

An optimal type of surgical treatment of the said conditions is implantation of fixing material providing a recovery for supporting pelvic floor organs.

The most important aspect of surgery is a necessity of I level support repair (apical fixation of cervix or vaginal vault). Many authors have shown a key role for axial cervix support fixation of pelvic floor organs in a physiological position (Summers A., Winkel L. A., Hussain H. K., DeLancey J. O. The relationship between anterior and apical compartment support. Am J Obstet Gynecol. 2006; 194(5): 1438-1443; Chen L., Ashton-Miller J. A., Hsu Y., DeLancey J. O. Interaction among apical support, levator ani impairment, and anterior vaginal wall prolapse. Obstet Gynecol. 2006; 108:324-332).

There are some methods providing axial support for pelvic floor structures, which have specific advantage and disadvantages.

1. Ligature fixation of vagina to the sacrospinal ligament is an effective method of apical prolapse repair. The main advantage is absence of an implanted mesh material, which excludes mesh-associated postsurgical complications. The main disadvantages are the following: a need of a wide tissue dissection for access to the sacrospinal ligament is a technical difficulty, lateralization and tension of vagina at fixation result to a high risk of developing a pain syndrome and dyspareunia. A conventional case of the operation supposes hysterectomy, which causes additional risks (Paraiso M. F., Ballard L. A., Walters M. D., Lee J. C., Mitchinson A. R. Pelvic support defects and visceral and sexual function in women treated with sacrospinous ligament suspension and pelvic reconstruction. Am J Obstet Gynecol. 1996; 175(6):1423-1431; Sze H. M., Karram M. M. Transvaginal repair of vault prolapse: a review. Obstet Gynecol. 1997; 89(3):466-475).

2. Sacrocolpopexy includes cervix or vaginal vault fixation with a mesh to the anterior longitudinal ligament of the spine in the sacrum area and it is performed via abdominal access. According to the Cochrane laboratory review, this method has shown a significant efficacy in patients having apical prolapse (Maher C., Feiner B., Baessler K., Christmann-Schmid C., Haya N., Brown J. Surgery for women with apical vaginal prolapse. Cochrane Database Syst Rev. 2016; 10:CD012376). The main advantages of the method are durable axial fixation and a possibility for uterine preservation. The disadvantages of sacrocolpopexy are a need of laparotomic or laparoscopic intraabdominal access, a dissection in the area of the sacral plexus, a long operation time, high requirements for a technical equipment to an operation room and qualification of a surgeon, complexity of simultaneous repair of II and III levels for support, high requirements to a patient somatic condition. Also, all the specific complications associated with implantation of a permanent synthetic mesh are intrinsic for this method.

3. Transvaginal prosthetic reconstruction of the pelvic floor with sacrospinal fixation includes implantation of the mesh through the sacrospinal ligaments and its fixation to the cervix or the vaginal vault. The advantage of this approach is a possibility of simultaneous precise and durable repair of II and III levels for support, which is effective, the simplest for carrying out and undemanding to a special equipment. A pain syndrome after this type of surgery is met much rarer than after ligature fixation to the sacrospinal ligaments due to a tension-free fixation of apical structures. However, presence of the permanent implanted mesh material is also associated with specific complications: erosions and chronic pain syndrome.

According to studies performed earlier, a permanent presence of mesh causes development of complications, most of which are directly associated with an excess amount of the implanted material as well as its textile structure. On literature data, incidence of the described complications can achieve 33% (Falagas M. E., Velakoulis S., Iavazzo C., Athanasiou S. Mesh-related infections after pelvic organ prolapse repair surgery. Eur J Obstet Gynecol Reprod Biol. 2007; 134(2):147-156). Some authors mention relationship of erosion appearance mainly with properties of implants themselves as being a foreign body, they facilitate a development of a local inflammatory reaction and promotes formation of vaginal mucosal defects (Shah H. N., Badlani G. H. Mesh complications in female pelvic floor reconstructive surgery and their management: A systematic review. Indian J Urol. 2012; 28(2): 129-153).

Significant technical difficulties and respectively high intraoperative risks are caused by a removal of mesh in a case of development of complications. The problem is in a heavy ingrowth of fibrous tissues into a structure of the mesh implants that are multiple bound monofilament threads, removal of which is impossible by a simple traction or minimal dissection. In the case of ligature fixation the removal of threads from tissues or even simple cutting them is usually sufficient for cure.

Today there is a need to develop a method of pelvic floor repair, which would combine advantages of ligature fixation (safety and reversibility) and prosthetic surgery (minimal dissection, standardizing and physiological properties). Herewith, a novel approach should minimize a possibility for development of mesh-associated complications. Implementation of axial support should be carried out on a base of a minimal implanted material and a possibility of easy retraction of pelvic floor structures, which can be achieved by delivery of surgical ligatures unlinked between each other in an implantation area and arrangement thereof along fixation axis (axially). Therefore, development of a fully absorbable system for delivery of ligatures unlinked between each other, which are intended for axial fixation of pelvic floor organs, is based on a clinically and pathophysiologically based approach to prophylaxis of mesh-associated complications and maintenance of surgery efficacy.

Various modifications of meshes for pelvic floor repair are developed at present time (AU2012289928, publ. 6 Feb. 2014; U.S. Ser. No. 10/245,134, publ. 2 Apr. 2019; US2003191480, publ. 9 Oct. 2003; US20070282160, publ. 6 Dec. 2007). These implants are not universal and their application can lead to significant complications.

A mesh endoprosthesis TiGr-Matrix produced by Novus Scientific company (FDA K163005. URL: https://www.accessdata.fda.gov/cdrh_docs/pdf16/K163005.pdf, access date 13 Apr. 2020) is known, it is a composite film with thickness of 0.6-0.7 mm, made of fast- and slow-absorbing monofilament fibers. The fast-absorbing fibers consist of a copolymer of glycolide, lactide, and trimethylene carbonate and are approximately fully resorb for 4 months. The fibers with long term resorbing are made of a copolymer of glycolide and trimethylene; a time for full resorbing for them is about 3 years. The disadvantage of this mesh is its full absorption during 3 years, which can obviously lead to the recurrence due to disorganization of fibrous tissue after the disappearance of the foreign body in the tissues.

The mesh for surgical reconstruction of pelvic floor Prolift+M is known (Khandwala S., Jayachandran C. Transvaginal mesh surgery for pelvic organ prolapse—Prolift+M: a prospective clinical trial. Int Urogynecol J. 2011; 22(11): 1405-1411), which includes a central part linked seamlessly with fixing tapes. This implant is made of a partially absorbing composite mesh consisting of equal parts of non-absorbing polypropylene monofilament threads and absorbing poliglecaprone monofilament threads. After the degradation of absorbing component in 2-3 months the non-absorbable one that is left on place still has mesh textile structure but with much lower surface density. As the mesh is in the implantation site all mesh-associated complications can occur.

A surgical mesh Proflex (Proflex Mesh. URL: https://samyangbiopharm.com/eng/ProductIntroduce/medical_device02_01, access data 13.04.2020) for reconstruction of fascial defects is known. It is made of bicomponent monofilament thread consisting of fibers of two types: non-biodegradable polypropylene threads and biodegradable threads of a copolymers of glycolic acid and caprolactone. The said mesh has the same disadvantages as the previous described prototype.

A mesh endoprosthesis Vypro II (EP1520552B1) made of equal amount of biodegradable polyglactine and non-biodegradable polypropylene multifilament fiber is the closest prototype in a technical substance to the claimed system. After absorbing of polyglactine component the polypropylene net is left in the surgery site, it gives to the implant all disadvantages of non-resorbing net implants. The surgical mesh Vypro II is associated with a high incidence rate of postsurgical complications: detachment of the mesh from apical compartment (20%), extrusion of the net into a vaginal cavity (14%), development of implant-associated pelvic pain needed to retraction of the said surgical mesh (18%) among them. An observation time for patients was 1 year (Maher C., Baessler K., Glazener C. M. A., Adams E. J., Hagen S. Surgical management of pelvic organ prolapse in women: A short version Cochrane review. Neurourol Urodyn, 2008; 27(1):3-12; ElHaddad R., Martan A., Masata J., Svabik K., Koleska T. Long-term review on posterior-colporrhaphy with levator ani muscles plication and incorporating a Vypro II mesh. Ceska Gynekol. 2009; 74(4):282-285).

SUMMARY

The technical problem is a need to develop an effective ligature delivery system for axial fixation of pelvic floor structures in pelvic organ prolapse and stress urinary incontinence, which does not have the above disadvantages and has a wide number of applications.

The technical effect is providing the axial support that is physiological for apical structures of pelvic floor and minimizing risks of mesh-associated postsurgical complications.

The technical effect is achieved by that in the ligature delivery system for axial fixation of pelvic floor structures in pelvic organ prolapse and stress urinary incontinence, the mesh material is woven from a non-biodegradable and biodegradable monofilament threads, according to the invention so that non-biodegradable threads are arranged along to the implant axis and are not linked with each other.

It is known that a vector of abdominal pressure is directed top-down parallel to axial spinal axis in the pelvis region. A support of pelvic organs in apical region provides the sacrouterine cardinal attachment complex being incompetent in patients with genital prolapse. The presented invention acts function of axial support by replacement of function of a damaged attachment structures. In addition, the invention can be used for providing a physiological support of urethra at treatment of stress urinary incontinence in women by creating so called «hammock» instead of damaged fascia of a urogenital diaphragm. Therefore, in comparison with the prototype, the claimed invention more physiologically provides extensional (axial) support of apical compartment of pelvic floor and decrease of a risk for appearance of postsurgical complications.

BRIEF DESCRIPTION OF THE DRAWINGS

The claimed invention is explained with figures, wherein in

FIG. 1 the general view of the claimed system is shown, in

DETAILED DESCRIPTION OF THE PREFERRED EMBODIMENT

Figure 1:
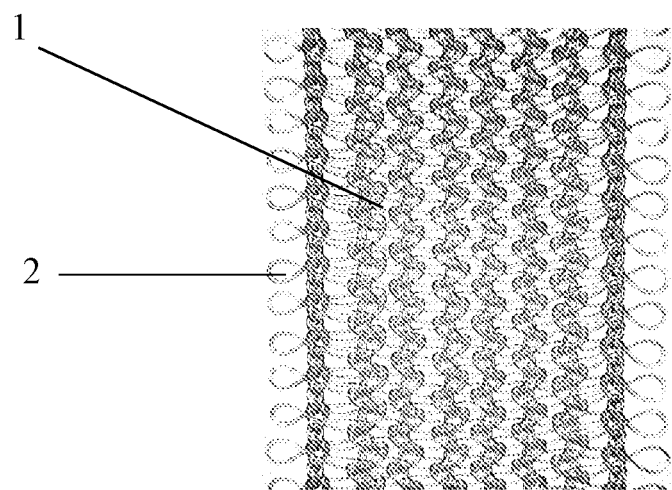
Figure 2:
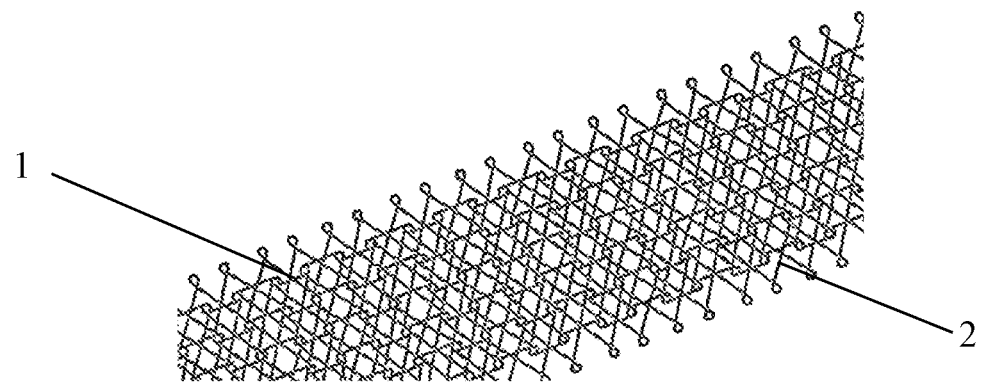
FIGS. 2 and 3 a structure of the claimed system before and after degradation of biodegradable threads is shown.
Figure 3:
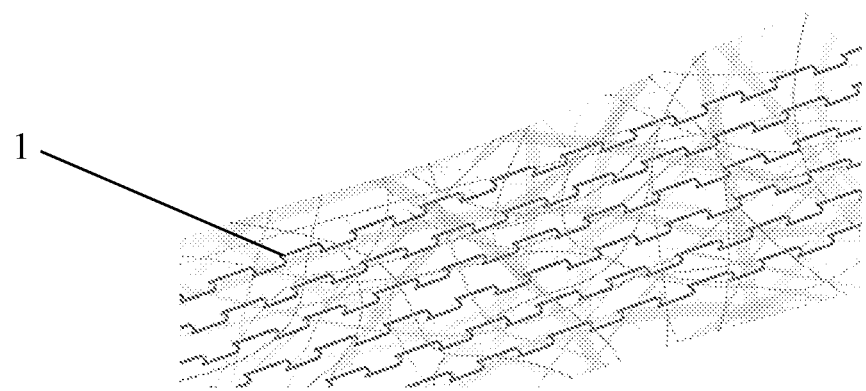
Figure 4:
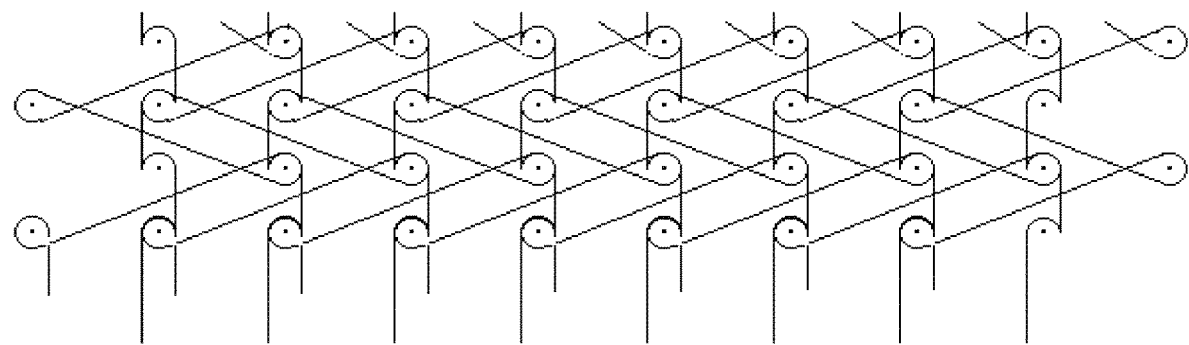
FIGS. 4 and 5 shows a graphic sign of intertangling before and after degradation of biodegradable threads.
Figure 5:
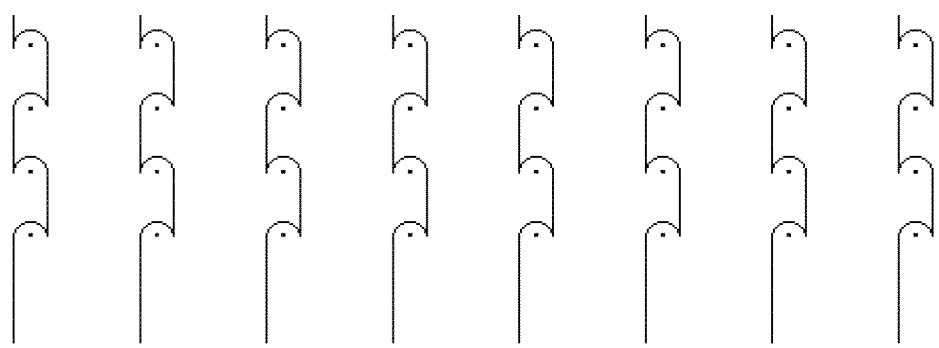

A ligature delivery system for axial fixation of pelvic floor structures in pelvic organ prolapse and stress urinary incontinence includes a woven mesh material made from non-biodegradable threads 1 and biodegradable threads 2, wherein the both types of threads are monofilament. Biodegradable threads 2 are arranged in both axial and cross-axial directions of the implant. Non-biodegradable threads 1 are arranged only axial to the implant length and are not linked to each other. In the most preferable embodiment polypropylene (hereinafter—«PP») monofilament thread of diameter of 0.06-0.12 mm is used as non-biodegradable thread 1. Also, in the most preferable embodiment, polydioxanone (hereinafter—«PDO») monofilament thread of diameter of 0.125-0.135 mm is used as non-biodegradable thread 2 arranged axial and cross-axial in the implant. The said ranges of thread thicknesses provides a balance between a strength of the article and convenience for implantation thereof and functioning in postoperative term, and in some cases these parameters beyond the said limits can be used in the scope of the claimed invention.

The claimed invention is implemented and can be reproduced many times on a warp knit machine equipped with tube needles and two threading combs, working of which is described in analytical sign: first 1/0; 4/5; second 0/1; 1/0, wherein a volume of threading of the both threading combs is 50% (in 1 threading needle). The first threading comb includes 8 monofilament threads of PDO, the second one includes 8 monofilament threads of PP. At the end of knitting thermostabilisation at the temperature of 105° C., pre-sterilisation alcohol treatment, drying with filtered air, packing and final sterilization with ethylene oxide are carried out. The main technical characteristics are in the table below

TABLE 1 the main technical characteristics of the article

| Parameter | Value |
|---|---|
| Width, mm | 12-13 |
| Stitch number in horizontal, stitches/100 mm | 60-65 |
| Stitch number in vertical, stitches/100 mm | 140-160 |
| Surface density, g/m$^2$ | 239-245 |
| Breaking force, N | 81-85 |
| Breaking elongation, % | 92-95 |
| If the length if implant is 45 cm, Diameter of PP monofilament threads of 0.06 mm, diameter of PDO monofilament threads of 0.12 mm: | |
| 1. weight of article, g | 1.84 |
| 1. weight of non-biodegradable (PP) monofilament threads, g | 0.06 |
| 1. weight of biodegradable (PDO) monofilament threads, g | 1.78 |

For apical prolapse repair in women the claimed invention is used in the following way.

A patient is on a surgical table in lithotomy position. After antiseptic treatment of surgical area and installation of urethral catheter, under general anesthesia dissection of anterior vaginal wall is performed. Subfascial dissection of paravaginal tissues in the direction of the sacrospinal ligaments is carried out. In dependence on a clinical situation and degree of manifestation of apical prolapse it is possible to carry out one-way (unilateral) or two-way (bilateral) fixation of the invention into the sacrospinal ligament. The special curved trocar is used for delivery of the invention in implantation field. The fixation of the invention to the cervix or the vaginal vault is performed with a non-resorbing surgical thread. After the implantation of the ligature delivery system the colporrhaphy and/or vaginal vault fixation are carried out. Surgical wound is closed.

Axial fixation in apical prolapse with the invention can be made by laparotomic and laparoscopic access, besides vaginal access.

In the embodiment for delivery of the invention in mid-urethral area at stress urinary incontinence in women the invention is used in the following way.

A patient is on a surgical table in lithotomy position. After antiseptic treatment of surgical field and installation of urethral catheter, under general anesthesia dissection of anterior vaginal wall in the mid urethral projection. The dissection of paravaginal tissues is performed in the direction of upper side of the inferior pubic ramus from both sides. The special curved trocar is used for delivery of the invention into an implantation area by perforation of structures of obturator complex (musculus obturator internus, obturator membrane and external obturator muscle). Therefore, the invention is arranged under mid urethra with forming «hammock», providing a physiological axial support the mid urethra instead of incompetent fascia. Surgical wound is closed.

Axial fixation at stress urinary incontinence with the invention can be made by retropubic access, besides transobturator one.

The claimed invention is explained with clinical examples.

Example 1

A patient is the woman B., 66 year. The complaints on foreign body feeling in vagina, vaginal prolapse were presented. The apical pelvic organ prolapse of stage 3 (Baden-Walker) is diagnosed. After carrying out the required diagnostic maneuvers it is made the decision on carrying out the treatment including apical fixation using the claimed invention (ligature delivery system with PP thread of diameter of 0.06 mm, PDO thread of diameter of 0.125 mm) via laparoscopic sacrocolpopexy.

The operation was successfully performed by the method described (Meriwether K V, Gold K P, de Tayrac R, Cichowski S B, Minassian V A, Cartwright R, Miotla P, Grimes C L, Brito L G O, Bazi T M, Carberry C L, Zhu L, Rogers R G. Joint report on terminology for surgical procedures to treat pelvic organ prolapse. Int Urogynecol J. 2020; 31(3):429-463). The postsurgical term was without complications. She was released from hospital. At control reviews in two and six months after the operation the patient mentioned a well-being, complaints were not presented. At the review a good anatomic effect from the operation is noted (genital prolapse recurrence is not noted), postsurgical complications are not revealed.

Example 2

A patient is the woman I., 68 years. The complaints on vaginal wall prolapse and cervix uterine prolapse at physical activity were presented. The apical pelvic organ prolapse of stage 3 (Baden-Walker) is diagnosed. After carrying out the required diagnostic maneuvers it is made the decision on carrying out the treatment including apical fixation using the claimed invention (ligature delivery system with PP thread of diameter of 0.08 mm, PDO thread of diameter of 0.130 mm) via laparoscopic colposacropexy.

The operation was successfully performed by the method described (Meriwether K V, Gold K P, de Tayrac R, Cichowski S B, Minassian V A, Cartwright R, Miotla P, Grimes C L, Brito L G O, Bazi T M, Carberry C L, Zhu L, Rogers R G. Joint report on terminology for surgical procedures to treat pelvic organ prolapse. Int Urogynecol J. 2020 March; 31(3):429-463). The postsurgical term was without complications. She was released from hospital. At control reviews in two and six months after the operation the patient mentioned a well-being, complaints were not presented. At the review a good anatomic effect from the operation is noted (genital prolapse recurrence is not noted), postsurgical complications are not revealed.

Example 3

A patient is the woman N., 75 years. The complaints on foreign body felling in vagina, vaginal prolapse were presented. The anterior apical pelvic organ prolapse of stage 3 (Baden-Walker) is diagnosed. After carrying out the required diagnostic maneuvers it is made the decision to carry out the treatment including a hybrid reconstruction of pelvic floor with the claimed invention (ligature delivery system with PP thread of diameter of 0.10 mm, PDO thread of diameter of 0.130 mm) via transvaginal access.

The operation was successfully performed by the method described (Shkarupa, D., Kubin, N., Shapovalova, E. et al. The resurrection of sacrospinous fixation: unilateral apical sling hysteropexy. Int Urogynecol J. 2020; 31:351-357). The postsurgical term was without complications. She was released from hospital. At control reviews in two and six months after the operation the patient mentioned a well-being, complaints were not presented. At the review a good anatomic effect from the operation is noted (genital prolapse recurrence is not noted), postsurgical complications are not revealed.

Example 4

A patient is the woman J., 70 years. The complaints on vaginal prolapse causing determined discomfort and stranguria were presented. In past medical history total hysterectomy on pelvic organ prolapse was noted, the recurrence was in 6 months. The posthysterectomy pelvic organ prolapse of stage 3 (Baden-Walker) is diagnosed. After carrying out the required diagnostic maneuvers it is made the decision to carry out the treatment including a hybrid reconstruction of pelvic floor with the claimed invention (ligature delivery system with PP thread of diameter of 0.12 mm, PDO thread of diameter of 0.135 mm) via transvaginal access.

The operation was successfully performed by the method described (Shkarupa D, Kubin N, Shapovalova E, Zaytseva A, Pisarev A, Staroseltseva O. The novel technique of post-hysterectomy vaginal vault prolapse repair: Apical sling and "neocervix" formation. Eur J Obstet Gynecol Reprod Biol. 2017; 214:11-15). The postsurgical term was without complications. She was released from hospital. At control reviews in two and six months after the operation the patient mentioned a well-being, complaints were not presented. At the review a good anatomic effect from the operation is noted (genital prolapse recurrence is not noted), postsurgical complications are not revealed.

Example 5

A patient is the woman K., 45 years. The complaints on urinary incontinence upon coughing, sneezing, physical activity were presented. The stress urinary incontinence is diagnosed. After carrying out the required diagnostic maneuvers it is made the decision to carry out the treatment including implantation of the claimed invention (ligature delivery system with PP thread of diameter of 0.08 mm, PDO thread of diameter of 0.125 mm) under mid urethra via transobturator access.

The operation was successfully performed by the method described (Shkarupa D, Kubin N, Staroseltseva O, Shapovalova E. Adjustable transobturator sling for the treatment of primary stress urinary incontinence. Int Urogynecol J. 2018; 29(9):1341-1347). The postsurgical term was without complications. She was released from hospital. At control reviews in two and six months after the operation the patient mentioned a well-being, she noted an absence of urinary loss episodes. The coughing stress test was negative at the review, postsurgical complications are not revealed.

Example 6

A patient is the woman O., 42 years. The complaints on urinary incontinence upon coughing, sneezing, physical activity, body disposition were presented. The stress urinary incontinence is diagnosed. After carrying out the required diagnostic maneuvers it is made the decision to carry out the treatment including implantation of the claimed invention (ligature delivery system with PP thread of diameter of 0.06 mm, PDO thread of diameter of 0.125 mm) under mid urethra via retropubic access.

The operation was successfully made on the method described (Valderrama V, Collins S A, Swift S, Jha S, Rosamilia A, de Tayrac R. Joint report on the terminology for surgical procedures to treat stress urinary incontinence in women. Int Urogynecol J. 2020; 31(3):465-478). The postsurgical term was without complications. She was released from hospital. At control reviews in two and six months after the operation the patient did not present any complaints, she noted an absence of urinary loss episodes. The coughing stress test was negative at the review, postsurgical complications are not revealed.

What is claimed is:

1. An implantable mesh for axial fixation of pelvic floor structures in pelvic organ prolapse and stress urinary incontinence, comprising:
   a plurality of non-biodegradable monofilament threads; and
   a plurality of biodegradable monofilament threads interknitted with the plurality of non-biodegradable monofilament threads;
   wherein each of the plurality of biodegradable monofilament threads is arranged in both an axial direction and a cross-axial direction of the implantable mesh, and each of the plurality of non-biodegradable monofilament threads is arranged in the axial direction of the implantable mesh;
   wherein the plurality of non-biodegradable monofilament threads comprises non-biodegradable monofilament threads that are not linked with each other; and
   wherein each of the plurality of non-biodegradable threads is made of polypropylene and has a diameter of 0.06-0.12 mm, and each of the plurality of biodegradable threads is made of polydioxanone and has a diameter of 0.125-0.135 mm.

* * * * *